(12) United States Patent
Bilderback

(10) Patent No.: US 7,822,177 B2
(45) Date of Patent: Oct. 26, 2010

(54) BACK-REFLECTION X-RAY CRYSTALLOGRAPHY METHOD AND SYSTEM

(75) Inventor: Donald H. Bilderback, Ithaca, NY (US)

(73) Assignee: Multiwire Laboratories, Ltd., Ithaca, NY (US)

( * ) Notice: Subject to any disclaimer, the term of this patent is extended or adjusted under 35 U.S.C. 154(b) by 56 days.

(21) Appl. No.: 12/328,382

(22) Filed: Dec. 4, 2008

(65) Prior Publication Data

US 2010/0142679 A1  Jun. 10, 2010

(51) Int. Cl.
*G01N 23/203* (2006.01)
(52) U.S. Cl. ........................................................ 378/76
(58) Field of Classification Search .................... 378/71, 378/73, 76, 79, 81
See application file for complete search history.

(56) References Cited

U.S. PATENT DOCUMENTS 5,073,918 A * 12/1991 Kamon ........................ 378/71

* cited by examiner

*Primary Examiner*—Chih-Cheng G Kao
(74) *Attorney, Agent, or Firm*—Fox Rothschild LLP; Gary Hecht; Perry M. Fonseca

(57) ABSTRACT

Provided is a method and system for back-reflection X-ray diffraction of a specimen that yields the orientation of a crystalline sample in a quick and an automated way. The method includes setting an approximate pre-selected X-ray detector to specimen distance, subjecting the specimen to X-rays, recording the Laue diffraction pattern, calculating the Miller indices of a fraction of the spots in the resulting pattern, averaging the Miller indices, moving a virtual representation of the specimen by a small amount along a line connecting the film to the specimen, changing the film-to-specimen distance, repeating the calculation, averaging and moving in small angular steps until the virtual representation of the specimen has been moved through a small distance range and best fits to the observed data, and determining the optimum film-to-specimen distance resulting in the smallest average Miller index.

20 Claims, 8 Drawing Sheets

Sample's Parameters

- 501 — Det.-to-Spec. Distance: [150.0]   Spot Radius: [6]
- 502 — Collect Time (seconds): [10]   KV: [18]
- Error Bar (2.0 max): [1.50]   mA: [16]
- Epsilon: [6.00]   Stereo Mag: [1.2]
- 503 — Max Miller Index in Stereo:   H: [2]   K: [2]   L: [2]
- Max Miller Index in Find HKL:   H: [6]   K: [6]   L: [F]

Sample Name: [sapphire on end of sample]
Operator: [mw]
Comments: [2 mm collimator]

[Cancel]  [OK]

<<Press F1 for HELP>>

Fault Tolerance   [×]

- Percentage of Bad Points allowed: [20] — 601
- Maximum film to specimen deviation [millimeters]: [2.00] — 602
- Step Size [millimeters]: [1.00] — 603
- 604 — ☑ Stop looking at different distances after a solution has been found
- ☐ Stop looking after any solution has been found
- 605 — ☑ Optimize the orientation matrix

[Cancel]  [OK]

<<Press F1 for HELP>>

700

800

BACK-REFLECTION X-RAY CRYSTALLOGRAPHY METHOD AND SYSTEM

FIELD OF THE INVENTION

This invention generally relates to a method and system of X-ray crystallography, and, more particularly, to a method and system of back-reflection X-ray crystallography utilizing an automated X-ray detector.

BACKGROUND OF THE INVENTION

X-ray crystallography is a method of determining the arrangement of atoms within a crystal, in which a beam of X-rays strikes a crystal and scatters into many different directions. From the angles and intensities of these scattered beams, a crystallographer can produce a three-dimensional picture of the density of electrons within the crystal. From this electron density, the mean positions of the atoms in the crystal can be determined, as well as their chemical bonds, their disorder and sundry other information.

Since very many materials can form crystals—such as salts, metals, minerals, semiconductors, as well as various inorganic, organic and biological molecules—X-ray crystallography has been fundamental in the development of many scientific fields. In its first decades of use, this method determined the size of atoms, the lengths and types of chemical bonds, and the atomic-scale differences among various materials, especially minerals and alloys. The method also revealed the structure and functioning of many biological molecules, including vitamins, drugs, proteins and nucleic acids such as DNA. X-ray crystallography is still a chief method for characterizing the atomic structure of new materials and in discerning materials that appear similar by other experiments. X-ray crystal structures can also account for unusual electronic or elastic properties of a material, shed light on chemical interactions and processes, or serve as the basis for designing pharmaceuticals against diseases.

Crystals are regular arrays of atoms, and X-rays can be considered waves of electromagnetic radiation. Atoms scatter X-ray waves, primarily through the atoms' electrons. Just as an ocean wave striking a lighthouse produces secondary circular waves emanating from the lighthouse, so an X-ray striking an electron produces secondary spherical waves emanating from the electron. This phenomenon is known as scattering, and the electron is known as the scatterer. A regular array of scatterers produces a regular array of spherical waves. Although these waves cancel one another out in most directions (destructive interference), they add constructively in a few specific directions, determined by Bragg's law, $2d \sin\theta = n\lambda$, where n is any integer. These specific directions appear as spots on the diffraction pattern, often called reflections. Thus, X-ray diffraction results from an electromagnetic wave (the X-ray) impinging on a regular array of scatterers, the repeating arrangement of atoms within the crystal.

X-rays are used to produce the diffraction pattern because their wavelength $\lambda$ is typically the same order of magnitude (1-100 Ångströms) as the spacing d between planes in the crystal. In principle, any wave impinging on a regular array of scatterers produces diffraction. To produce significant diffraction, the spacing between the scatterers and the wavelength of the impinging wave should be roughly similar in size.

The idea that crystals could be used as a diffraction grating for X-rays arose in 1912 in a conversation between Paul Peter Ewald and Max von Laue in the English Garden in Munich. Ewald had proposed a resonator model of crystals for his thesis, but this model could not be validated using visible light, since the wavelength was much larger than the spacing between the resonators. Von Laue realized that electromagnetic radiation of a shorter wavelength was needed to observe such small spacings, and suggested that X-rays might have a wavelength comparable to the unit-cell spacing in crystals. Von Laue worked with two technicians, Walter Friedrich and his assistant Paul Knipping, to shine a beam of X-rays through a sphalerite crystal and record its diffraction on a photographic plate. After being developed, the plate showed a large number of well-defined spots arranged in a pattern of intersecting circles around the spot produced by the central beam, now referred to as a Laue image. Von Laue developed a mathematical relationship that connects the scattering angles and the size and orientation of the unit-cell spacings in the crystal.

In a typical X-ray crystallography system, after a crystal specimen has been obtained, the specimen is mounted on a goniometer and gradually rotated while being bombarded with X-rays, producing a diffraction pattern, or oscillation (or rotation) image of regularly spaced known spots. The two-dimensional images taken at different rotations are converted into a three-dimensional model of the density of electrons within the crystal using the mathematical method of Fourier transforms, and combined with chemical data known for the sample. Poor resolution or even errors may result if the crystals are too small, or not uniform enough in their internal makeup.

X-ray crystallography is related to several other methods for determining atomic structures. Similar diffraction patterns can be produced by scattering electrons or neutrons, which are likewise interpreted using a Fourier transform. If single crystals of sufficient size cannot be obtained, various X-ray scattering methods can be applied to obtain less detailed information.

There are two ways of performing X-ray crystallography using Laue images. In transmission Laue systems, the film or X-ray detector is placed behind the crystal specimen to record X-ray beams which are transmitted through the crystal. In back-reflection Laue systems, also generally referred to herein as "back-reflection X-ray detectors", the actual film or X-ray detector is placed between the X-ray source and the crystal specimen. Thus, the X-ray beams which are diffracted in a backwards direction are recorded.

Therefore, in a back-reflection X-ray detector, the X-ray source is on the same side of the specimen as the film or detector onto which the Laue images are reflected. This arrangement provides for a compact size relative to a transmission X-ray detector system. Back-reflection geometry is also the only universal method for thick samples of more than a mm thickness, such as boules of silicon, turbine blades, etc which are too thick to penetrate with 10 to 30 keV x-rays.

Back-reflection X-ray crystallography has recently increased in importance in manufacturing, particularly in the area of electronic devices incorporating thin crystals, for example in laser optical devices, such as CD or DVD players, and the like. It is very important in the manufacturing environment that X-ray detectors be able to quickly and automatically obtain and analyze Laue images to determine, for example, optimal specimen orientation for industrial applications of the specimen. The relatively compact nature of a back-reflection X-ray detector renders it suitable to numerous manufacturing applications.

The Multiwire Laboratories MWL110™ X-ray detector is an example of an X-ray detector which quickly collects a back-reflection Laue image for analysis. The Laue image typically contains 6 to 30 spots that, if properly analyzed, will tell how the rows and columns of atoms lined up in the crystal are oriented with respect to the X-ray beam that creates the image. This is usually the information the user is looking for, so as to enable sample rotation using a two or three axis rotation stage, or goniometer, to bring the sample into proper alignment for the application at hand.

In typical usage, the Laue spots are "indexed" or named with three integer numbers called "Miller indices", which describes the fixed angular relationship between the planes. The information needed is contained in a mathematical 3 by 3 matrix called the Orientation Matrix. The Orientation Matrix provides a complete description of the unit cell of the crystal in question as well as its angular alignment with respect to the x-ray beam.

Several difficulties have arisen in the typical usage of back-reflection X-ray crystallography, some of which are referred to here.

Determination of the Miller index tends to be sensitive to measurement of the angle between spots on a Laue image, which, in turn is sensitive to the "film-to-specimen" distance. In a typical application, the film-to-specimen distance ranges from 125 mm to 175 mm. If the specimen is not over the center of the rotary stage of the goniometer, this distance can easily change by a few mm during sample rotation. If the film-to-specimen distance is off by a couple of mm, then the measurement of the angle, for example say 10 degrees, between two spots will be off, complicating the generation of Miller indexing of the spots. Thus, the user would have to know enough crystallography to judge if the resulting Miller index is correct or not.

Next, typical X-ray detectors require a user to identify points on the Laue image to identify the center of spots. Typically, the user had to manually select all the spots to be indexed in the Laue image, and the first two spots selected had to be in an "indexing table". Thus, there is a need for an X-ray detector to automatically detect the center of spots on a Laue image.

Also, in prior art X-ray detectors, the user had to index 100% of the points selected. If there was a "bad" point, for example, one with a higher Miller index than allowed by the MaxHKL setting, or "noise", etc., then expert intervention would normally be required to operate the detector. The expert would typically need to be very knowledgeable about crystallography and experienced in indexing a Laue image. This is not a desirable situation, particularly in a manufacturing environment. Thus, there is a need for an X-ray detection system that can automatically tolerate such bad points and still arrive at the correct answer by ignoring a small fraction of the "bad" points.

In prior art X-ray detection systems, the user could typically spend significant time manually selecting spots by hand before finding those which were in an indexing table. Thus, there is a need for a system that automatically cycles through all the various possible combinations of spots, determining all possible orientation matrices and select those with the lowest average Miller index.

Additionally, X-ray detectors to date have fitted the orientation matrix to just the first two points selected. Thus, there is a need for a detector that automatically fits the orientation matrix to all the Laue image data points, not just the first two points that were used to create the orientation matrix. This would allow for a more accurate orientation matrix than if it were built only from the first two points selected by the user.

There is also a need for an X-ray detector that provides for creation of "macros", or pre-determined sequences of steps which automate entire sequences of collecting Laue images, finding spots, generating Miller indices, and determining orientation. These macros would be particularly useful in manufacturing environments.

It would also be useful for an X-ray detector to allow the user to specify and highlight additional planes of interest, even if they are behind the collimator, and thus not "seen" by the detector.

In prior X-ray detectors, a single maximum value could typically be provided for the planes H, K and L. In cases where the "unit cell" vectors differ greatly in length, such as with quartz, where the c-axis is about twice the length of the a-axis, there is a need for an X-ray detector that allows three independent maximal values for H, K and L, such as Hmax, Kmax and Lmax.

Typical X-ray detectors allow Miller indexing of only one or, at most, very few planes. Thus, it is desirable to provide an X-ray detector that allows for indexing all the visible planes in the image, even for those having high Miller index, for example, planes indices that vary from 0-15.

Also, for rhombohedral unit cells, those in which a=b=c, alpha=beta=gamma, and which are not 90 degrees, e.g., 56.3 degrees, there is a need for an X-ray detector which indexes in rhombohedral coordinates, but displays in hexagonal coordinates. This feature would result in more positive indexing as transformation converts the rhombohedral HKLs into Hexagonal form that humans understand more readily. The indexing in rhombohedral coordinates is more reliable because the Miller indices are lower than in the hexagonal case.

SUMMARY OF THE INVENTION

An aspect of the present invention provides a method and system of back-reflection X-ray diffraction of a specimen, including setting an approximate pre-selected X-ray detector to specimen distance (hereafter called "film-to-specimen distance"), subjecting the specimen to X-rays, recording the back-reflected Laue diffraction pattern, calculating the Miller indices of a predetermined fraction of the spots in the resulting pattern, averaging the Miller indices of the fraction of spots, moving a virtual representation of the specimen by a predetermined small amount along a line connecting the film to the specimen, changing the film-to-specimen distance, repeating the calculation, averaging and moving in small angular steps until the virtual representation of the specimen has been moved through a predetermined small distance range and best fits to the observed data, and determining the optimum film-to-specimen distance resulting in the smallest average Miller index.

In another aspect of the invention, the preselected x-ray detector to specimen distance is in a range corresponding to 0 to 60 degrees for points in opposing corners of a detector screen.

In one aspect of the invention, the virtual representation of the specimen is moved along the line of the incident x-ray beam and results in a change of film-to-specimen distance by an amount of 0 millimeters to 2 millimeters.

In another aspect of the invention, the predetermined fraction of spots for which Miller indices are calculated is less than 100%.

In another aspect of the invention, the predetermined fraction of spots for which Miller indices are calculated is between 75% and 85%.

In one aspect of the invention, all possible combinations of starting planes are used in an indexing table when detecting the pattern, and selecting the starting planes which yield the lowest average Miller index of the indexed Laue pattern.

In another aspect of the invention, each of the Miller indices H, K and L have individual maximum values Hmax, Kmax and Lmax, respectively.

In one aspect of the invention, Miller indices are calculated for up to 20 extra planes of interest so that a spot that is hidden by the collimator when perfectly oriented is made visible in the center of the Laue pattern.

In another aspect of the invention, Miller indices are assigned indices from 0-15.

In another aspect of the invention, the orientation matrix is optimized by performing a least squares fit to all the spots of the diffraction pattern by rocking the orientation matrix by small angles along three orthogonal axes for a best fit.

An aspect of the present invention provides a method and system of back-reflection X-ray diffraction of a specimen, including subjecting the specimen to X-rays, recording the back-reflected diffraction pattern, automatically detecting the points of the pattern to determine the center of gravity of each of the observed diffraction spots.

BRIEF DESCRIPTION OF THE DRAWINGS

FIG. 5 is a Parameters Box 500 that shows how the detector-to-specimen distance is set to a particular value, in accordance with an embodiment of the present invention;

FIG. 6 is a Fault Tolerance panel, in accordance with an embodiment of the present invention;

DETAILED DESCRIPTION

Figure 1:
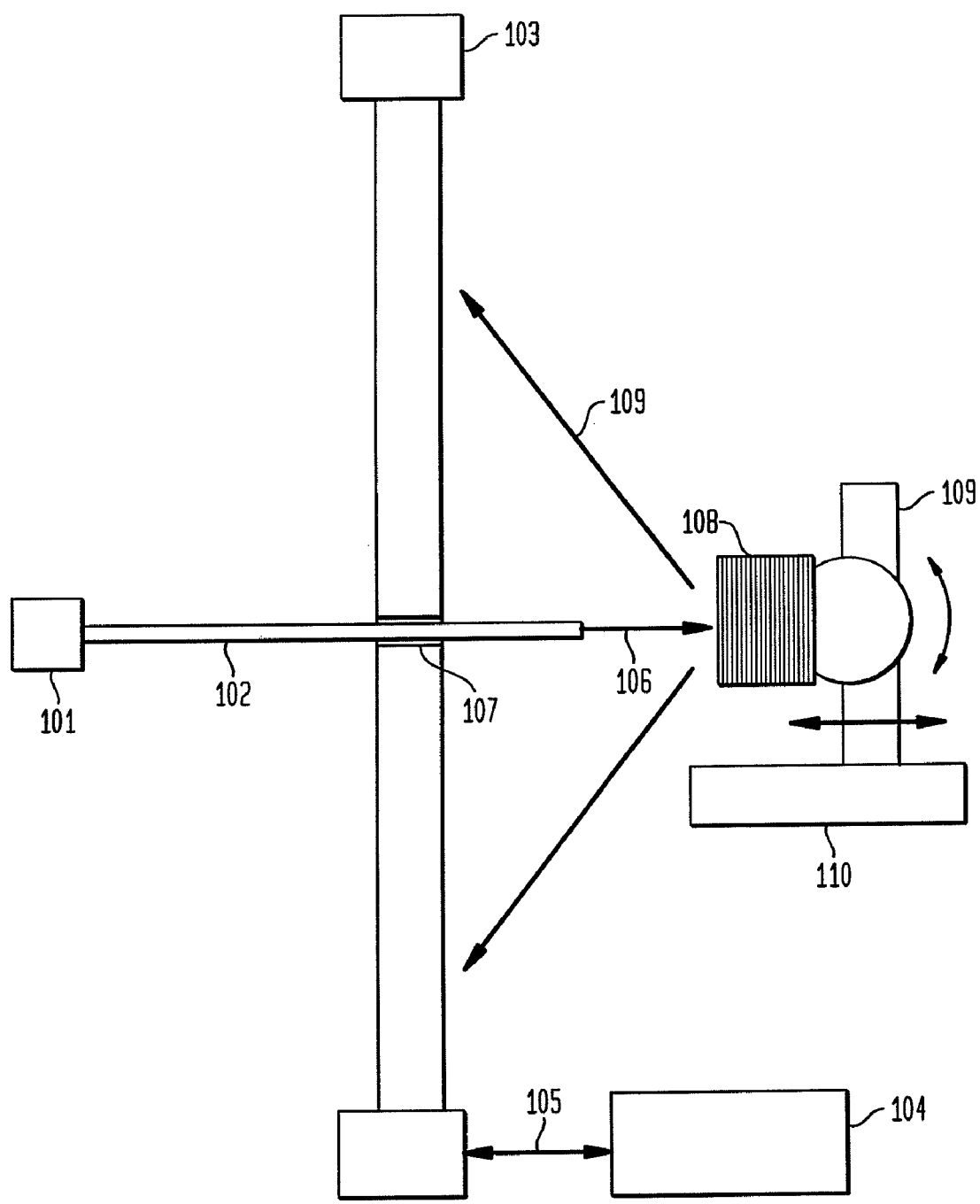
FIG. 1 is a schematic diagram illustrating a back-reflection X-ray crystallography system, in accordance with an embodiment of the present invention.

In the following description, for purposes of explanation, specific numbers, materials and configurations are set forth in order to provide a thorough understanding of the invention. It will be apparent, however, to one having ordinary skill in the art, that the invention may be practiced without these specific details. In some instances, well-known features may be omitted or simplified so as not to obscure the present invention. Furthermore, reference in the specification to "one embodiment" or "an embodiment" means that a particular feature, structure or characteristic described in connection with the embodiment is included in at least one embodiment of the invention. The appearances of the phrase "in an embodiment" in various places in the specification are not necessarily all referring to the same embodiment.

The term "film-to-specimen distance" referred to in the descriptions of various embodiments of the invention herein described is intended to generally describe the distance from the specimen being analyzed and the detector screen 103.

As used herein, the terms "computer" or "computer system" refers to any commonly used computer device having at least a processor, associated memory, and one or more input device, without limitation. A computer used in the X-ray detector of the present invention is typically, but not necessarily housed with the detector, and is operatively connected to the detector's components. Examples of computers include, but are not limited to, desktop computers, laptop computers, minicomputers, mobile devices, cellular telephones, and others. It is assumed all computers described herein incorporate an appropriate operating system, any additional necessary software and any necessary communication interfaces.

Similarly, communication between system elements, for example, in figure item 105, is assumed to be over conventional communication lines and interfaces, without limitation.

The present invention advantageously provides a method and system for X-ray crystallography which adjusts the film-to-sample distance by small steps, such as 0.5 mm to 1mm, over a small distance range, such as + or –5 mm, making simulated Laue images at each position to compare to the one Laue image taken of the crystal, calculating and displaying the best solution, the one with smallest average Miller index.

The present invention also advantageously provides an X-ray detector that automatically detects the center of spots on the Laue image.

The present invention also advantageously provides an X-ray detector that allows for a user to only need to correctly index a percentage, such as say 80% of points in a Laue image, to get a unique and correct solution. For example, if you have 30 points in the image, up to 6 points or 20% can have too high a Miller index, yet the X-ray detector of the present invention will tolerate these "bad points" or "non-indexable points" and still come up with the correct solution. This "fault-tolerance" in the indexing procedure removes a lot of present day frustration by general users of the equipment.

The present invention also advantageously provides an X-ray detector that methodically cycles through all the possible combinations and finds all the orientation matrices possible. The present invention also advantageously provides for automated computer sorting through all the different solutions and picking the one with the lowest average Miller index, which generally gives the correct answer desired.

The present invention also advantageously provides an X-ray detector that automatically fits the orientation matrix to all the Laue image data points, not just the first two points that were used to create the orientation matrix. This allows for a more accurate orientation matrix than if it were built only from the first two points selected by the user.

The present invention also advantageously provides an X-ray detector that provides for creation of "macros", or pre-determined sequences of steps which automate entire sequences of collecting Laue images, finding spots, generating Miller indices, and determining orientation.

The present invention also advantageously provides an X-ray detector that allows the user to specify and highlight additional planes of interest, even if they are behind the collimator, and thus not "seen" by the detector. In the present invention, using the "Find Extra Plane" feature, the user can specify up to 10 planes of interest to be highlighted in the indexed solution in a different color, even if it is behind the collimator. Misorientation of the desired plane, the answer you are looking for, is automatically given in degrees at the bottom of the image. For example, one frustration of novice users is that if you wanted a "100" orientation of a cubic crystal, i.e., the orientation of the face of the edge of a cubic crystal such as silicon, the user would find other HKs that weren't 100 located around the actual "100" that is not visible because it is located along the direction of the incoming x-ray beam and can't be seen by the detector. In the present invention, the calculated Orient Matrix may be used to mathematically show the user where it "should" be, including all the statistics of how far out from orientation it really is from perfect alignment.

The present invention also advantageously provides an X-ray detector that allows three independent maximal values for H, K and L, such as Hmax Kmax and Lmax. This allows for a more powerful index table generator, and is of advantage when the unit cell vectors describing the unit cell significantly differ in length from each other such as for sapphire crystals where the c-axis is about twice the length of the a-axis length. It generally allows for improved control over the indexing process. For example, the user may also now directly type in Miller indices of any two planes and begin the indexing manually, which is of great use in situations involving a "tough" pattern to be indexed for the first time.

The present invention also advantageously provides an X-ray detector that allows for indexing planes, having, for example, Miller indices over the range of 0-15.

The present invention also advantageously provides an X-ray detector that allows, with respect to rhombohedral unit cells, those in which a=b=c, alpha=beta=gamma, and which are not 90 degrees, e.g., 56.3 degrees, for indexing in rhombohedral coordinates, and displaying in hexagonal coordinates. This feature generally results in more positive indexing as transformation converts the rhombohedral HKLs into the Hexagonal form more readily understood by humans.

FIG. 1 is a schematic depiction of an exemplary back-reflection X-ray crystallography system 100. In a preferred embodiment of the invention, the system includes an X-ray source 101, a collimator 102, a detector screen 103 that has a hole through its center to pass the collimator, and a goniometer 109. The goniometer 109 can change the sample angle with respect to the X-ray beam in three orthogonal directions (one of them shown here). The system 100 further includes a computer 104 in operative communication 105 with the detector system. In a preferred embodiment, the computer 104, through its software and communication channels, controls and monitors the system components, so that they operate in a coordinated fashion. It is understood that, throughout this description, reference is made to "the detector" as performing steps of embodiments of the invention. These references are understood to involve the computer 104, its communication devices, and its processing hardware and software, without limitation. Computer 104 may be integrated with the detector screen 103 or a separate discrete component in communication with the detector screen 103.

Figure 4:
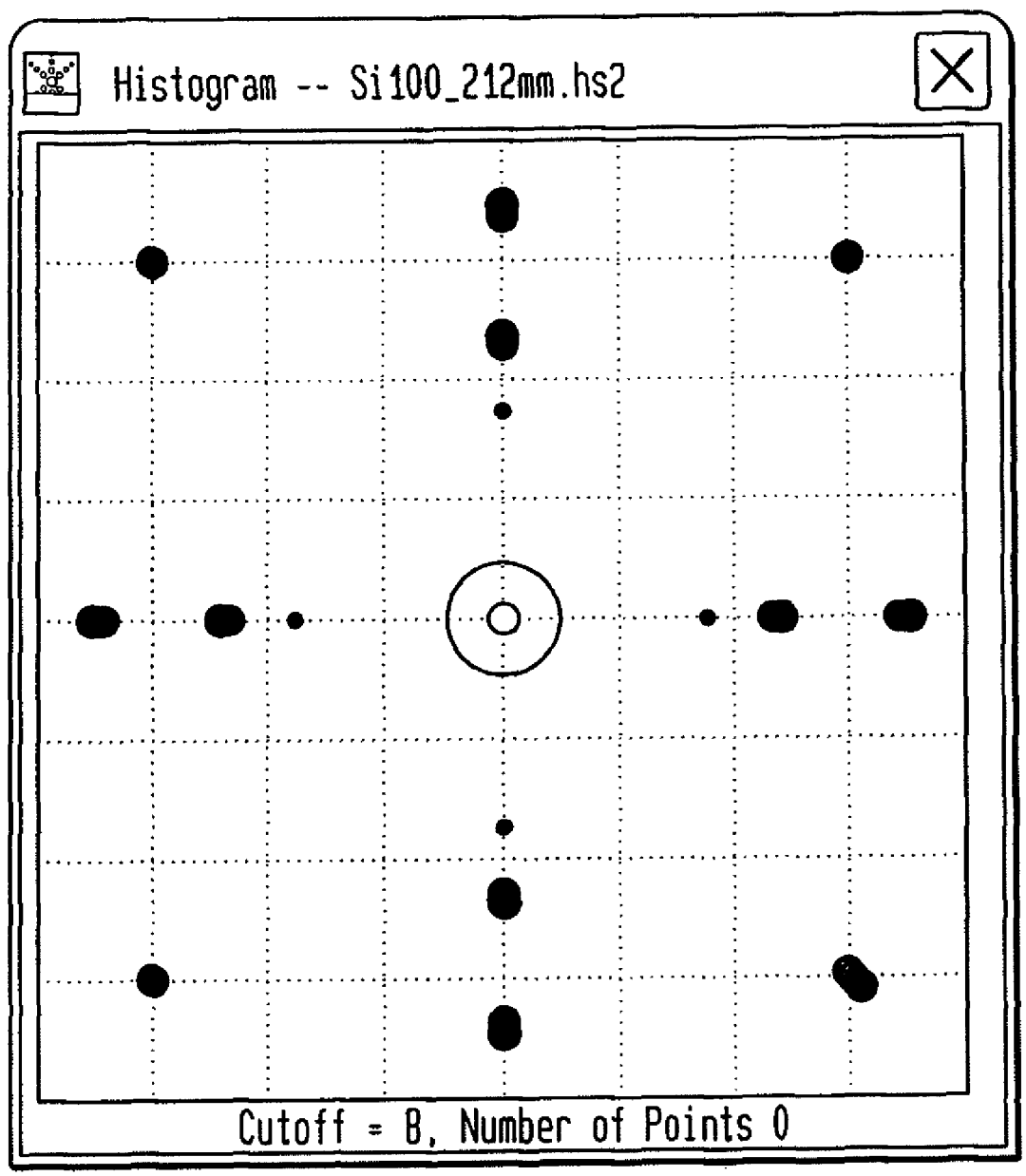
FIG. 4 is a Laue image, in accordance with an embodiment of the present invention.

The system 100 includes an X-ray source 101. X-ray sources are well known in the art, and it is generally preferable to use a polychromatic X-ray source, generally with a Tungsten target. In an embodiment, the X-rays 106 pass from the X-ray source 101 through a collimator 102, which serves to define the X-rays into a more pencil-like beam, which passes through a hole 107 in the detector screen 103, then encountering the specimen 108. Diffracted X-rays 109 are then back-scattered onto the detector screen 103, which then registers a Laue image as shown in FIG. 4.

The computer 104, itself under the control of a user (not depicted), controls the timing and other variables of the process. After the detector screen 103 registers the back-scattered X-rays 109, the computer 104 reads the Laue image data into its memory, where the data is further processed.

The system also includes a goniometer 109, on which the specimen to be examined is mounted. The goniometer 109 is also used in an embodiment of the invention to rotate the specimen with precision about its spatial axes. Also, the goniometer 109 may either be integrated with or mounted on a track 110, which may then be used to change or set the "film-to-specimen distance", or the distance from the detector 103 to the specimen, usually measured in millimeters. The goniometer 109 is manually slid along the track 110 to change this distance in the direction of the double arrow shown on 110.

Figure 2:
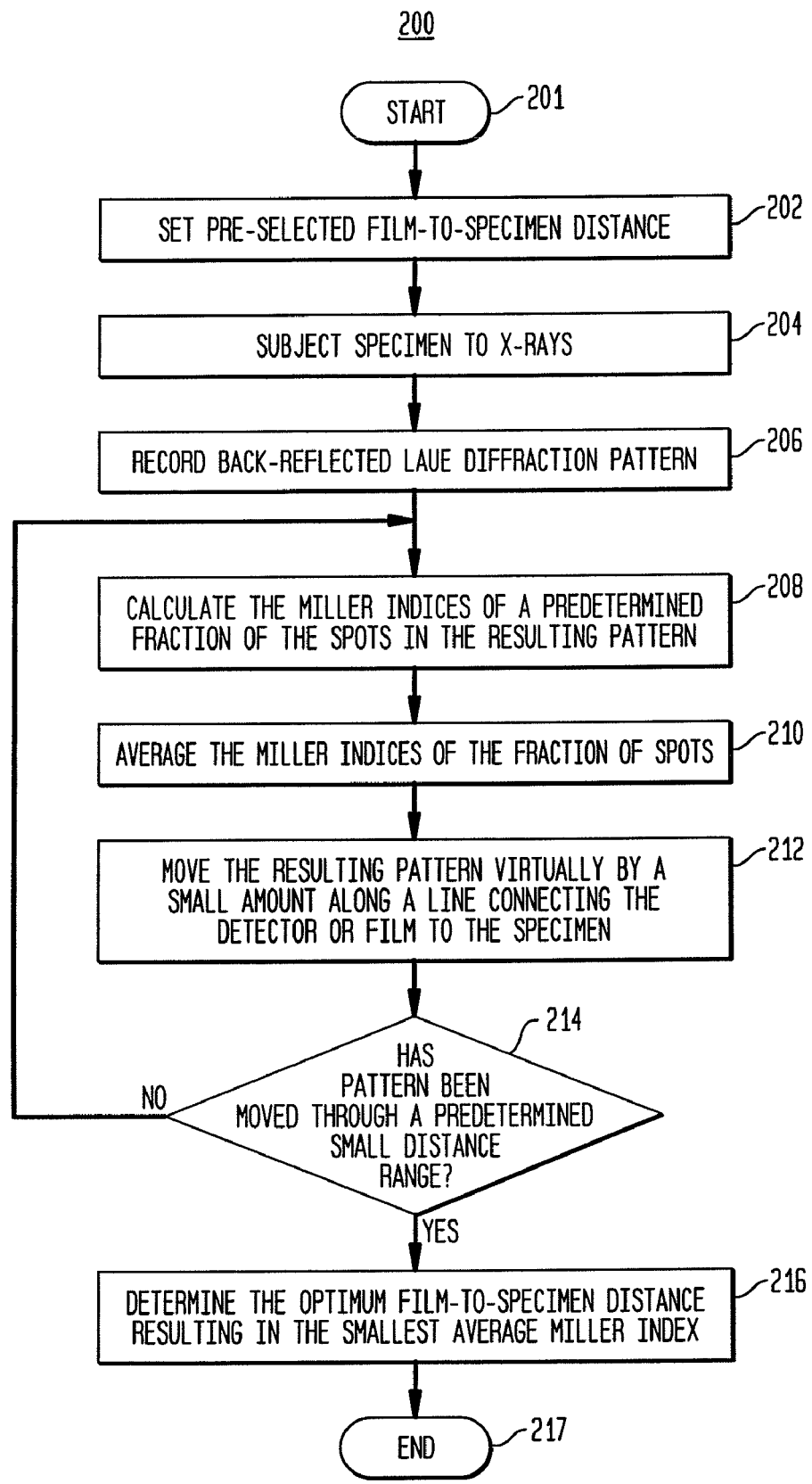
FIG. 2 is a flowchart depicting a method of automatically determining the optimum film-to-specimen distance in back-reflection X-ray crystallography, in accordance with an embodiment of the present invention

FIG. 2 is a flowchart depicting an exemplary method of automatically determining the optimum film-to-specimen distance in back-reflection X-ray crystallography. In an embodiment of the present invention, a user sets an approximate pre-selected X-ray detector to specimen distance, hereafter also called "film-to-specimen distance" 202. Next the specimen is subjected X-rays 204. After the back-reflected Laue diffraction pattern is recorded 206, Miller indices of a predetermined fraction of the spots in the resulting pattern are calculated 208, and averaged for a fraction of the spots 210. Next, a virtual representation of the specimen is moved by a predetermined small amount along a line connecting the detector to the specimen, thereby virtually changing the film-to-specimen distance 212.

Subsequently, the calculation, averaging and virtual moving steps are repeated until the virtual representation of the specimen has been moved through a predetermined small distance range 214. Next, the optimum film-to-specimen distance resulting in the smallest average Miller index is determined 216.

Figure 3:
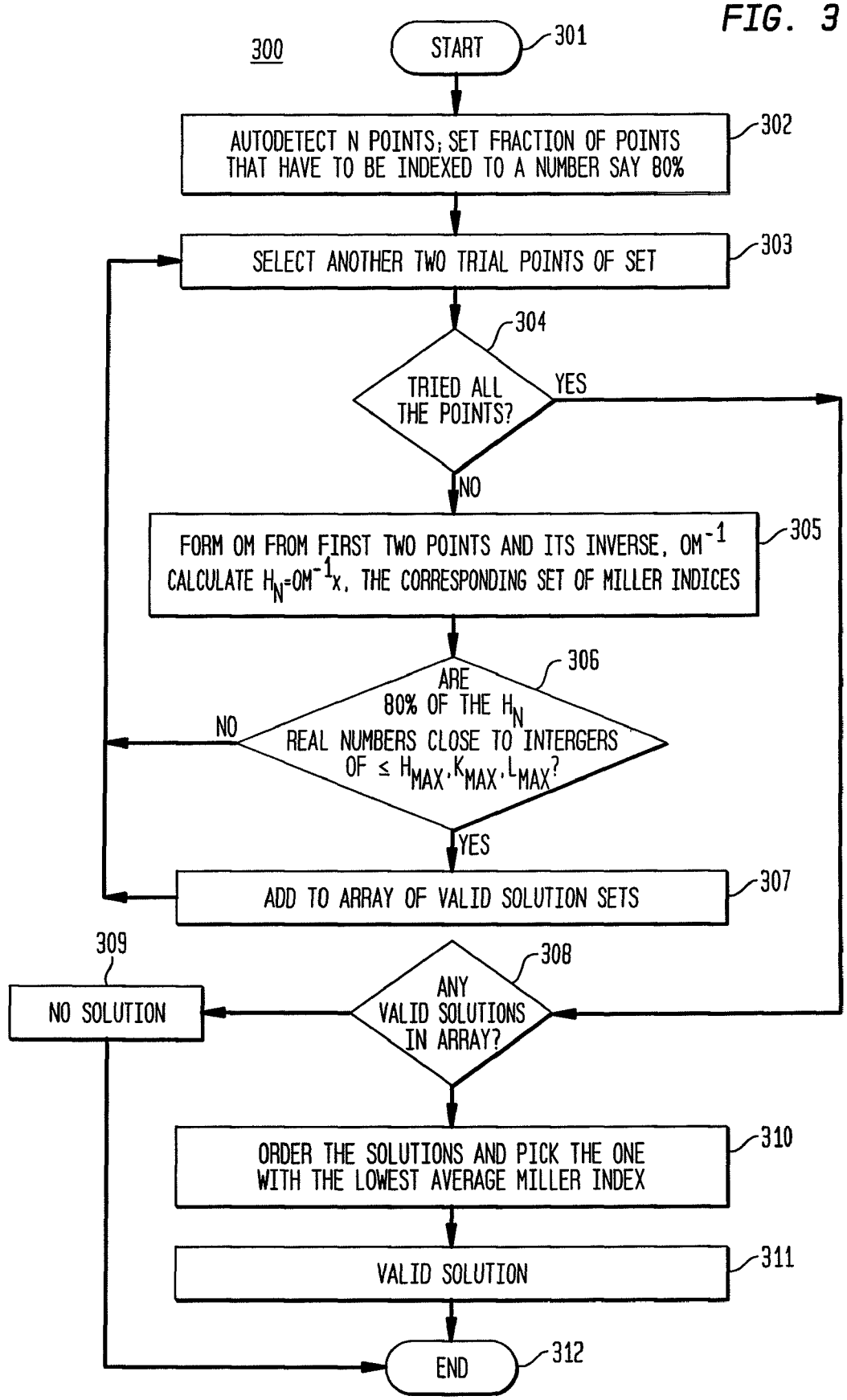
FIG. 3 is a flowchart depicting a method of Fault-Tolerant indexing of spots to turn them into Miller indices, in accordance with an embodiment of the present invention.

FIG. 3 is a flowchart depicting an exemplary method of Fault-Tolerant indexing of spots to turn them into Miller indices 300. After starting the routine 301, the input is a Laue image where an auto-detect routine finds the points that have to be indexed, of number N, as well as a percentage of points that have to be indexed, such as 80%, 302. The next step 303 is to take 2 of the N points and form an orientation matrix (OM) from these two points. The initial assignment of Miller indices of these two points comes from a starting table of planes that were first created by the user. The 3×3 OM is then inverted, $OM^{-1}$. Then the Miller indices of $H_N$ are created through matrix multiplication, i.e. $H_N = OM^{-1} * X$ where X is the array of the remaining spot coordinates determined from the x-ray detector system. If the resulting $H_N$ real numbers are close to integer values, then the real numbers obtained from matrix multiplication can be rounded to integer values and checked to see if their H, K and L values are less than or equal to the values, $H_{MAX}$, $K_{MAX}$ and $L_{MAX}$, entered in the dialog box 305. If 80% of the $H_N$ entries or more are integer in form, then this OM solution is added to the array of valid solutions 307, and if not, more point combinations are tried until all the various point combinations are exhausted. At the end of this procedure, if there are no solutions in the solutions array, then a "No solution" message 309 is issued and the routine terminates. Nearly all the time, however, there are multiple solutions in the solutions array. These are ordered and one solution is picked, the one with the lowest average Miller index 310. This solution is labeled "Valid Solution" and the consequences of this version of the OM are displayed, such has how far out in angle (in degrees) is the desired diffraction plane (spot). Then the routine terminates 312 normally.

A result of the steps is that, in most cases, user or operator judgment in the use of the software analysis is now removed and automated tools can now completely determine the orientation of the Laue pattern and quantitatively display the misorientation angles of desired planes without user intervention.

In an embodiment of the present invention, the preselected x-ray detector to specimen distance is in a range corresponding to 0 to 60 degrees for points in opposing corners of the detector screen 103.

In an embodiment of the present invention, the virtual representation of the specimen is moved along the line of the incident x-ray beam and results in a change of film-to-specimen distance by an amount of approximately 0 millimeters to 2 millimeters.

In another embodiment, the predetermined fraction of spots for which Miller indices are calculated is less than 100%. In another embodiment, the predetermined fraction of spots for which Miller indices are calculated is between 75% and 85%. In an embodiment, a useful typical value is 80%, which makes the indexing of diffraction spots more fault-tolerant, i.e., not compromised by minor spot errors or by a spot with too high a Miller index for the setting of the analysis program.

In a further embodiment of the invention, the back-reflection X-ray diffraction method described above also includes using all possible combinations of starting planes in an indexing table when detecting the pattern, and selecting the starting planes which yield the lowest average Miller index.

Another aspect of the present invention in an embodiment provides for each of the Miller indices, H, K and L to have individual maximum values Hmax, Kmax and Lmax, respectively.

In another embodiment of the present invention, the above-described X-ray diffraction method also includes calculating Miller indices for up to 20 extra planes of interest so that a spot that is hidden by the collimator when perfectly oriented is made visible in the center of the Laue pattern.

In yet another embodiment of the invention, Miller indices ranging from 0 to 15 may be calculated and retained at one time.

In a further embodiment of the invention, the X-ray diffraction method described above further includes optimizing an orientation matrix by performing a least squares fit to all the spots of the diffraction pattern by rocking the orientation matrix by small angles along three orthogonal axes for a best fit.

Example 1, as shown in FIG. 5, shows an exemplary Parameters Box 500 that shows how the detector-to-specimen distance is set to 150 mm value 501. The Laue pattern is to be collected for a 10 second time interval 502 and the maximum Miller index in H, K and L is 6,6 and 15 (Hexadecimal value of "F") 503 is entered here. The max H,K and L values for Stereo refer to the making of the corresponding Stereographic projection from the actual Orientation Matrix determined from the Laue image.

Example 2, as shown in FIG. 6, depicts an exemplary Fault Tolerance panel 600. In this example, 20% of the points do not have to be indexable 601, a typical number. For the 150 mm distance given in Example 1, the actual detector-to-specimen distance is given, but a deviation of plus or minus 2 mm is selected 602 in this panel with step size of 1 mm 603 that looks for a "best match" with the actual observed Laue pattern from the x-ray detector 604. Also checked is the option to optimize the Orientation Matrix using all the indexable points observed through a least squares procedure 605.

Figure 7:
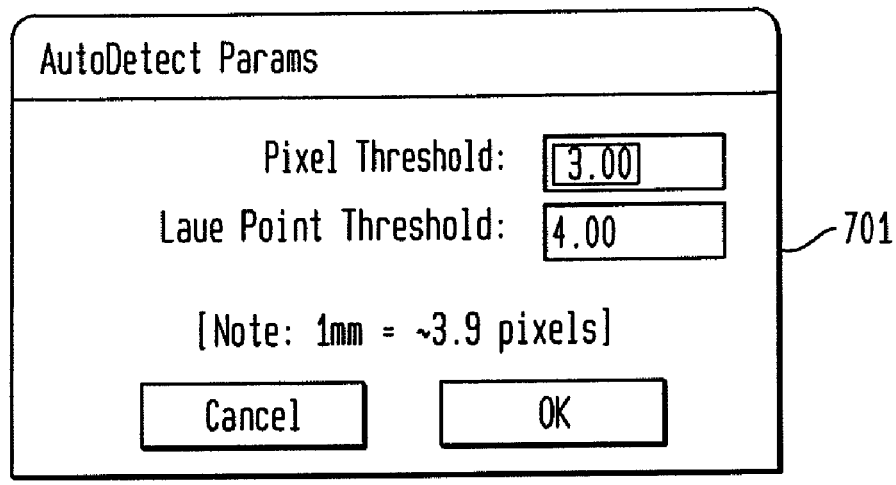
FIG. 7 is a AutoDetect Params box that controls the operation of the automatic peak finder to locate the center of gravity of each of the Laue spots, in accordance with an embodiment of the present invention.

Example 3, as depicted in FIG. 7, shows an exemplary AutoDetect Params box 700 that controls the operation of the automatic peak finder to locate the center of gravity of each of the Laue spots. The thresholds for determining the background and the signal levels in units of x-ray intensity are set here. The pixels that make up the Laue point, for instance, must have 4 counts (x-rays) 701 in at least one of the pixels for it to be found by the "peak finder" software.

Figure 8:
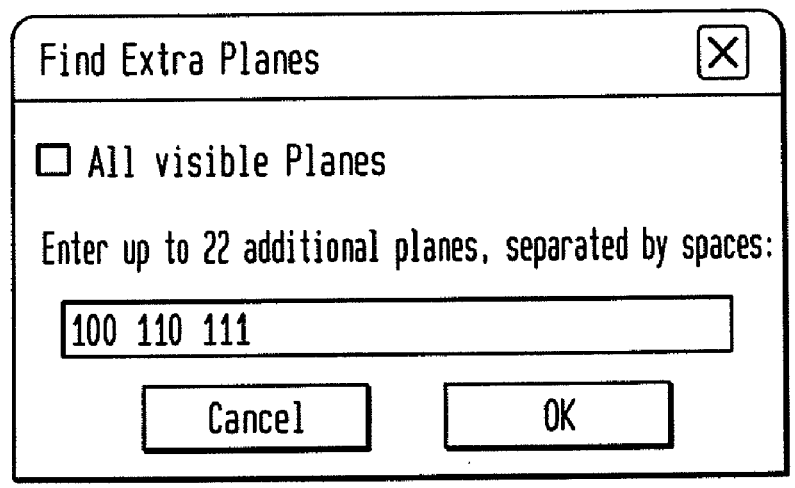
FIG. 8 is a dialog box for the Find Extra Planes feature, in accordance with an embodiment of the present invention.

Example 4, as depicted in FIG. 8, shows a exemplary dialog box 800 for the Find Extra Planes feature. This particular example shows the planes typically given for a cubic single crystal, the 100, 110 and 111 planes that show 4-fold, two-fold, and 3-fold symmetry.

Figure 9A:
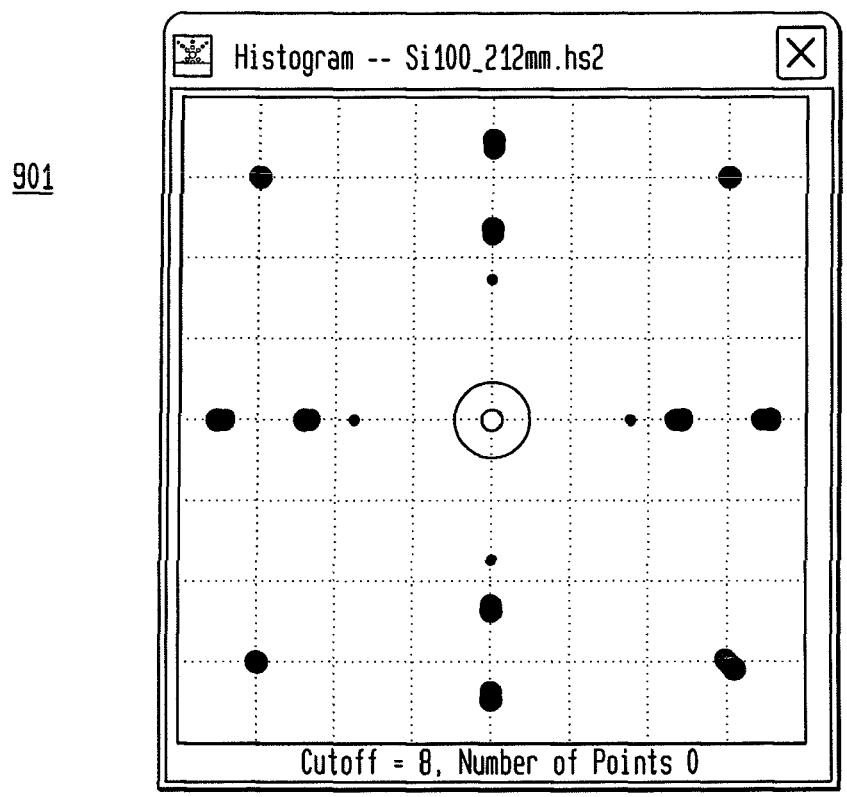
FIGS. 9(A) is a back-reflection Laue image of a silicon single crystal, in accordance with an embodiment of the invention.
Figure 9B:
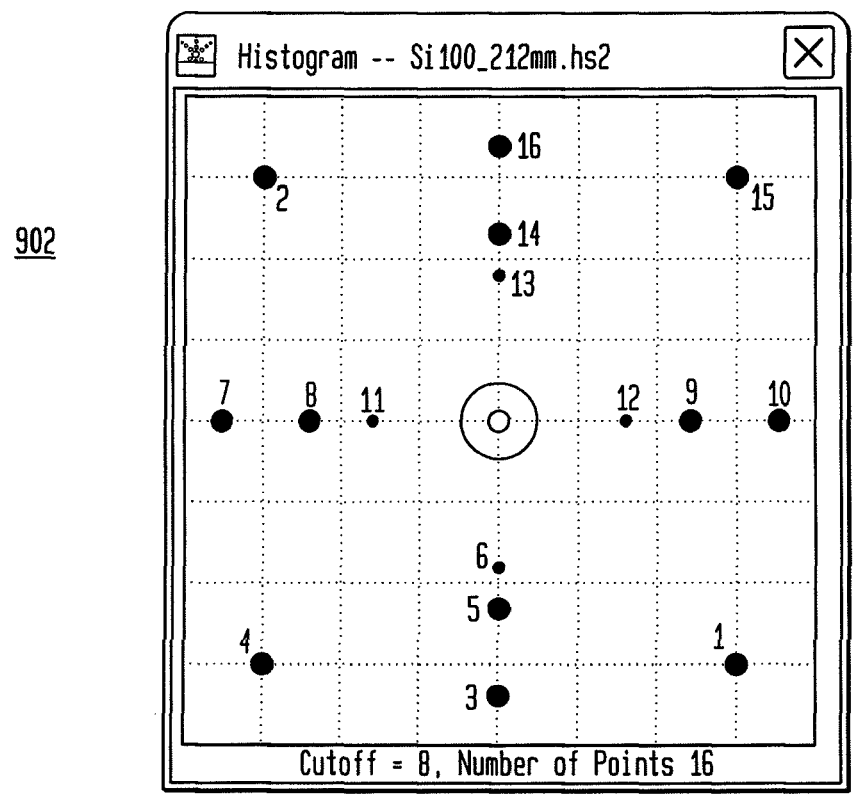
FIG. 9(B) depicts the results of a peak finder locates 16 spots and labeling them 1 through 16, in accordance with an embodiment of the invention.
Figure 9C:
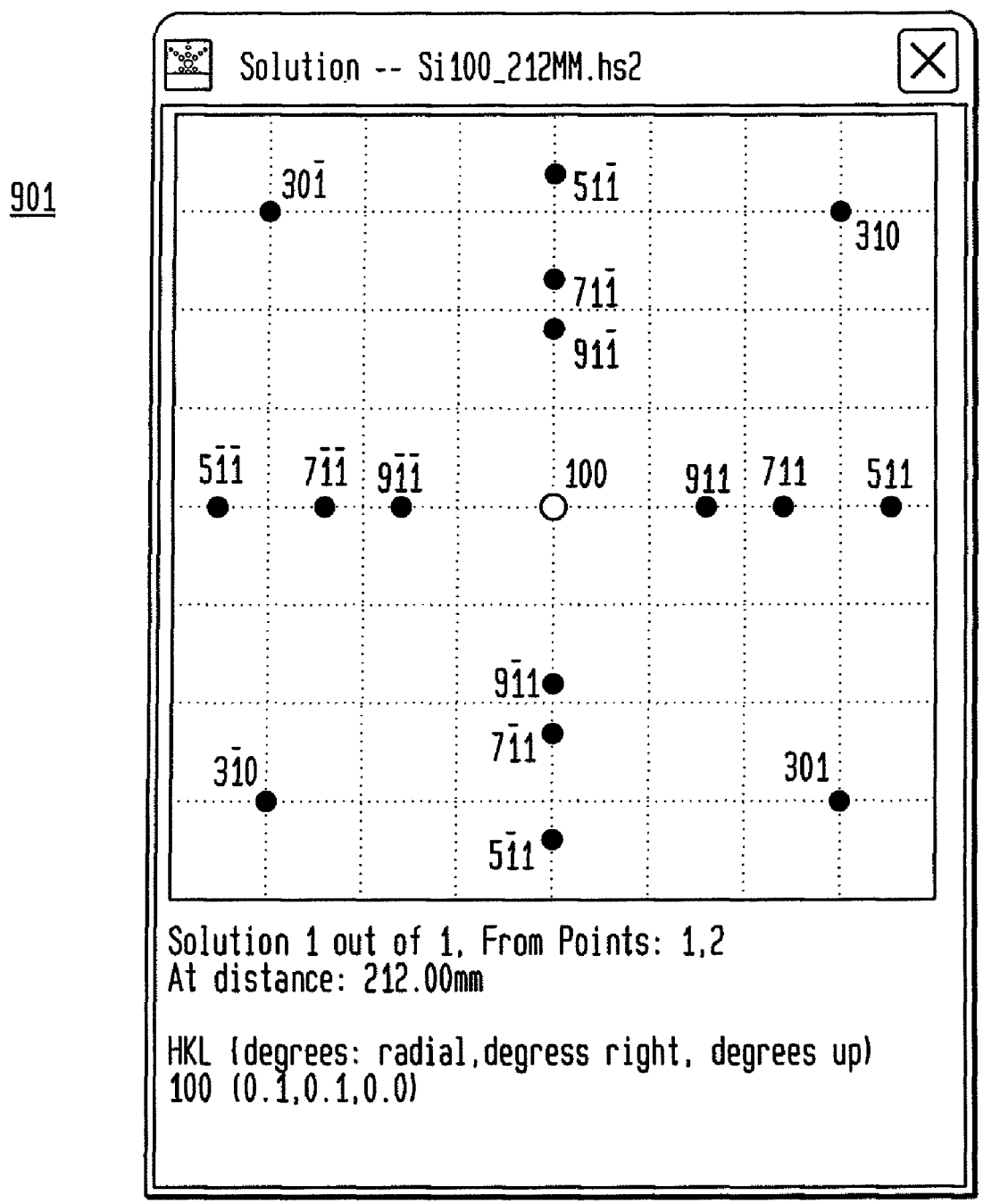
FIG. 9(C) depicts the results of calling the FindHKL routine to index the spots into the required Miller indices, in accordance with an embodiment of the invention.

Example 5, as depicted in exemplary FIGS. 9(A), 9(B) and 9(C), show the tools in action. First, a back-reflection Laue image 901 is taken with the x-rays on a silicon single crystal. Next we call for the peak finder that locates 16 spots and labels them 1 through 16, 902. Calling the FindHKL routine then indexes the spots into the required Miller indices show 903 that the spots have up to a maximum Miller index of 9. Note that the "100" spot, from the "100 orientation" can't be seen as it is along the direction of the incident x-ray beam. But the Orientation Matrix knows where this spot is, by virtue of knowing where its neighbors are located, and so can provide a calculated spot position (e.g., a large open spot in the center) to represent this spot. The angular mis-alignment is minimal. The detector system shows that the 100 spot is 0.1 degrees off perfect alignment horizontally and is perfectly aligned vertically (0.0). We independently know that this is the 100 by inspection "by eye" when the 4-fold pattern is observed, a property of the 100 orientation of a cubic crystal.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of back-reflection X-ray diffraction of a specimen, comprising:
    setting an approximate pre-selected X-ray detector to specimen distance (hereafter called "film-to-specimen distance");
    subjecting the specimen to X-rays;
    recording a back-reflected Laue diffraction pattern;
    calculating Miller indices of a predetermined fraction of spots in the resulting pattern;
    averaging the Miller indices of the fraction of spots;
    moving a virtual representation of the specimen by a predetermined small amount along a line connecting the film to the specimen, changing the film-to-specimen distance;
    repeating the calculation, averaging and moving in small angular steps until the virtual representation of the specimen has been moved through a predetermined small distance range and best fits to the observed data; and
    determining the optimum film-to-specimen distance resulting in the smallest average Miller index.

2. The back-reflection X-ray diffraction method according to claim 1, wherein the preselected x-ray detector to specimen distance is in a range corresponding to 0 to 60 degrees for points in opposing corners of a detector screen.

3. The back-reflection X-ray diffraction method according to claim 1, wherein the virtual representation of the specimen is moved along the line of the incident x-ray beam and results in a change of film-to-specimen distance by an amount of 0 millimeters to 2 millimeters.

4. The back-reflection X-ray diffraction method according to claim 1, wherein the predetermined fraction of spots for which Miller indices are calculated is less than 100%.

5. The back-reflection X-ray diffraction method according to claim 1, wherein the predetermined fraction of spots for which Miller indices are calculated is between 75% and 85%.

6. The back-reflection X-ray diffraction method according to claim 1, further comprising using all possible combinations of starting planes in an indexing table when detecting the pattern, and selecting the starting planes which yield the lowest average Miller index.

7. The back-reflection X-ray diffraction method according to claim 1, wherein each of Miller indices H, K and L have individual maximum values Hmax, Kmax and Lmax, respectively.

8. The back-reflection X-ray diffraction method according to claim 1, further comprising calculating Miller indices for up to 20 extra planes of interest so that a spot that is hidden by a collimator when perfectly oriented is made visible in the center of the Laue pattern.

9. The back-reflection X-ray diffraction method according to claim 1, further comprising calculating Miller indices for up to 16 planes.

10. The back-reflection X-ray diffraction method according to claim 1, further comprising optimizing an orientation matrix by performing a least squares fit to all the spots of the diffraction pattern by rocking the orientation matrix by small angles along three orthogonal axes for a best fit.

11. A back-reflection X-ray diffraction system comprising:
an X-ray generator;
a back-reflection Laue camera system comprising an X-ray detector, camera, base and three-axis rotation goniometer;
the X-ray generator and camera system being operatively connected to a computer system;
the computer system comprising a processor, computer memory, at least one input device, at least one display, the processor and memory configured to operate the X-ray generator and camera system to perform X-ray diffraction of a specimen by performing the steps of:
setting an approximate pre-selected X-ray detector to specimen distance (hereafter called "film-to-specimen distance");
subjecting the specimen to X-rays;
recording a back-reflected Laue diffraction pattern;
calculating Miller indices of a predetermined fraction of spots in the resulting pattern;
averaging the Miller indices of the fraction of spots;
moving a virtual representation of the specimen by a predetermined small amount along a line connecting the film to the specimen, changing the film-to-specimen distance;
repeating the calculation, averaging and moving in small angular steps until the virtual representation of the specimen has been moved through a predetermined small distance range and best fits to the observed data; and
determining the optimum film-to-specimen distance resulting in the smallest average Miller index.

12. The back-reflection X-ray diffraction system according to claim 11, wherein the preselected x-ray detector to specimen distance is in a range corresponding to 0 to 60 degrees for points in opposing corners of a detector screen.

13. The back-reflection X-ray diffraction system according to claim 11, wherein the virtual representation of the specimen is moved along the line of the incident x-ray beam and results in a change of film-to-specimen distance by an amount of 0 millimeters to 2 millimeters.

14. The back-reflection X-ray diffraction system according to claim 11, wherein the predetermined fraction of spots for which Miller indices are calculated is less than 100%.

15. The back-reflection X-ray diffraction system according to claim 11, wherein the predetermined fraction of spots for which Miller indices are calculated is between 75% and 85%.

16. The back-reflection X-ray diffraction system according to claim 11, further comprising using all possible combinations of starting planes in an indexing table when detecting the pattern, and selecting the starting planes which yield the lowest average Miller index.

17. The back-reflection X-ray diffraction system according to claim 11, wherein each of the Miller indices H, K and L have individual maximum values Hmax, Kmax and Lmax, respectively.

18. The back-reflection X-ray diffraction system according to claim 11, further comprising calculating Miller indices for up to 20 extra planes of interest so that a spot that is hidden by a collimator when perfectly oriented is made visible in the center of the Laue pattern.

19. The back-reflection X-ray diffraction system according to claim 11, further comprising calculating Miller indices over the range of 0 to 15.

20. The back-reflection X-ray diffraction system according to claim 11, further comprising optimizing an orientation matrix by performing a least squares fit to all the spots of the diffraction pattern by rocking the orientation matrix by small angles along three orthogonal axes for a best fit.

* * * * *